(12) United States Patent
Pinlac

(10) Patent No.: US 11,877,948 B2
(45) Date of Patent: Jan. 23, 2024

(54) EXTERNAL CATHETER

(71) Applicant: Rosemarie Pinlac, Holmdel, NJ (US)

(72) Inventor: Rosemarie Pinlac, Holmdel, NJ (US)

( * ) Notice: Subject to any disclaimer, the term of this patent is extended or adjusted under 35 U.S.C. 154(b) by 188 days.

(21) Appl. No.: 17/082,197

(22) Filed: Oct. 28, 2020

(65) Prior Publication Data

US 2021/0121318 A1    Apr. 29, 2021

Related U.S. Application Data

(60) Provisional application No. 62/927,257, filed on Oct. 29, 2019.

(51) Int. Cl.
*A61F 5/453*      (2006.01)
*A61F 5/441*      (2006.01)
*A61F 5/44*       (2006.01)

(52) U.S. Cl.
CPC .............. *A61F 5/453* (2013.01); *A61F 5/441* (2013.01); *A61F 5/4407* (2013.01)

(58) Field of Classification Search
CPC ...... A61F 5/453; A61F 5/4404; A61F 5/4408; A61F 5/443; A61F 5/44; A61F 5/441; A61F 5/451; A61F 5/445; A61F 6/04; A61F 5/4405; A61F 2005/4415; A61F 5/442; A62F 5/441
See application file for complete search history.

(56) References Cited

U.S. PATENT DOCUMENTS

| | | | | |
|---|---|---|---|---|
| 919,875 A * | 4/1909 | Johnson | ................... | A61F 5/453 604/289 |
| 3,523,537 A * | 8/1970 | Hill | ......................... | A61F 5/453 600/580 |
| 3,660,033 A * | 5/1972 | Schwartz | ................ | A61F 5/443 422/417 |
| 3,865,109 A * | 2/1975 | Elmore | ................... | A61F 5/441 604/339 |
| 4,022,213 A * | 5/1977 | Stein | ....................... | A61F 5/453 604/350 |
| 4,942,966 A * | 7/1990 | Kemp | ................... | B01L 3/5082 206/521 |

(Continued)

FOREIGN PATENT DOCUMENTS

| | | |
|---|---|---|
| CN | 104095698 A | 10/2014 |
| WO | 2010112028 A2 | 10/2010 |
| WO | 2011084018 A3 | 12/2011 |

*Primary Examiner* — Adam Marcetich
(74) *Attorney, Agent, or Firm* — Boudwin Intellectual Property Law, LLC; Daniel Boudwin

(57) ABSTRACT

An external catheter is provided. The external catheter has a planar base having a central aperture therethrough. A back surface of the planar base has an adhesive material that be used to removably secure the planar base of the device to the skin of a user. A tubular member is disposed on the front side of the planar base about the central aperture. The tubular member is composed of materials that enable fluid to be stored therein without leaking. A vent is disposed on the front surface of the tubular member to enable air to flow and reduce moisture in the area. A sealable drain located at a terminal end of the tubular member enables the fluid to be drained from the tubular member. The device can be used to capture and store bodily fluids and is especially useful for people who experience urinary incontinence.

16 Claims, 3 Drawing Sheets

(56) References Cited

U.S. PATENT DOCUMENTS

| | | | | |
|---|---|---|---|---|
| 5,078,707 | A | 1/1992 | Klug | |
| 6,551,293 | B1 * | 4/2003 | Mitchell | A61F 5/453 |
| | | | | 604/347 |
| 6,635,037 | B1 * | 10/2003 | Bennett | A61F 5/453 |
| | | | | 604/353 |
| 10,588,775 | B2 * | 3/2020 | Acosta | A61M 39/24 |
| 10,799,386 | B1 * | 10/2020 | Harrison, Sr. | A61F 5/441 |
| 11,389,320 | B2 * | 7/2022 | Mavrinac | A61F 5/453 |
| 2004/0176746 | A1 * | 9/2004 | Forral | A61F 5/453 |
| | | | | 604/544 |
| 2007/0269145 | A1 * | 11/2007 | Eisenbarth | B65D 88/1618 |
| | | | | 383/102 |
| 2009/0163883 | A1 * | 6/2009 | Christensen | A61F 5/441 |
| | | | | 604/328 |
| 2009/0259206 | A1 * | 10/2009 | Kai | A61F 5/4404 |
| | | | | 604/352 |
| 2013/0338617 | A1 * | 12/2013 | Newton, Jr. | A61F 5/453 |
| | | | | 604/353 |
| 2014/0350500 | A1 * | 11/2014 | Joseph | A61F 5/441 |
| | | | | 604/339 |
| 2015/0320583 | A1 * | 11/2015 | Harvie | A61F 5/441 |
| | | | | 604/351 |
| 2018/0098877 | A1 * | 4/2018 | Pierson | A61F 5/4405 |
| 2019/0247222 | A1 * | 8/2019 | Ecklund | A61F 5/453 |
| 2020/0375787 | A1 * | 12/2020 | Wang | A61F 5/453 |
| 2020/0397636 | A1 * | 12/2020 | Robinson | A61G 9/006 |

* cited by examiner

EXTERNAL CATHETER

CROSS REFERENCE TO RELATED APPLICATIONS

This application claims the benefit of U.S. Provisional Application No. 62/927,257 filed on Oct. 29, 2019. The above identified patent application is herein incorporated by reference in its entirety to provide continuity of disclosure.

BACKGROUND OF THE INVENTION

The present invention relates to catheters. More particularly, the present invention provides for an external catheter that can be removably secured to the groin area of a userin order to capture and store bodily fluids.

Many people suffer from urinary incontinence and related complications. If a urinary incident occurs, and the fluid is not captured, moisture can remain on the person's skin and clothing. This moisture can lead an increased risk of developing moisture related disorders and can cause pressure ulcers which are extremely painful. Additionally, the presence of moisture in the area of the wound results in a longer healing and recuperation time. Many times, these types of wounds can become worse before they begin to heal and get better. In some situations, a hospital stay is required to treat the condition, which can be expensive and time-consuming. Such hospital treatment often involves a traditional urinary catheter which can complicate the underlying issue and lead to a urinary tract infection. These compounding problems can be more and more painful and make urination even harder and painful.

Devices have been disclosed in the known art that relate to catheters. These include devices that have been patented and disclosed in patent application publications. However, the devices in the known art have several drawbacks. Traditional catheters typically require the services of a trained medical professional which can be expensive and inconvenient. Some catheters require an invasive medical procedure to be performed in a hospital setting. Even where care is taken, infections and other contracted ailments is not uncommon in such a setting. Some devices are used for urinary collection but are not designed to store bodily fluids for an extended period of time. Similarly, some devices are not designed to be worn for an extended period of time and may fall off if the weareroving around.

The present invention substantially diverges in design elements from the known art and consequently it is clear that there is a need in the art for an improvement to existing catheter devices. In this regard the present invention substantially fulfills these needs.

SUMMARY OF THE INVENTION

In view of the foregoing disadvantages inherent in the known types of catheters now present in the prior art, the present invention provides an external catheter wherein the same can be removably secured to the groin area of a user in order to capture and store bodily fluids. The present external catheter comprises a planar base having a central aperture therethrough. A back surface of the planar base has an adhesive material that can be used to removably secure the planar base of the device to the skin of a user. A tubular member is disposed on the front side of the planar base about the central aperture. The tubular member is composed of materials that enable fluid to be stored therein without leaking. A vent is disposed on the front surface of the tubular member to enable air to flow and reduce moisture in the area. A sealable drain located at a terminal end of the tubular member enables the fluid to be drained from the tubular member. The device can be used to capture and store bodily fluids and especially useful for people who experience urinary incontinence.

Other objects, features, and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
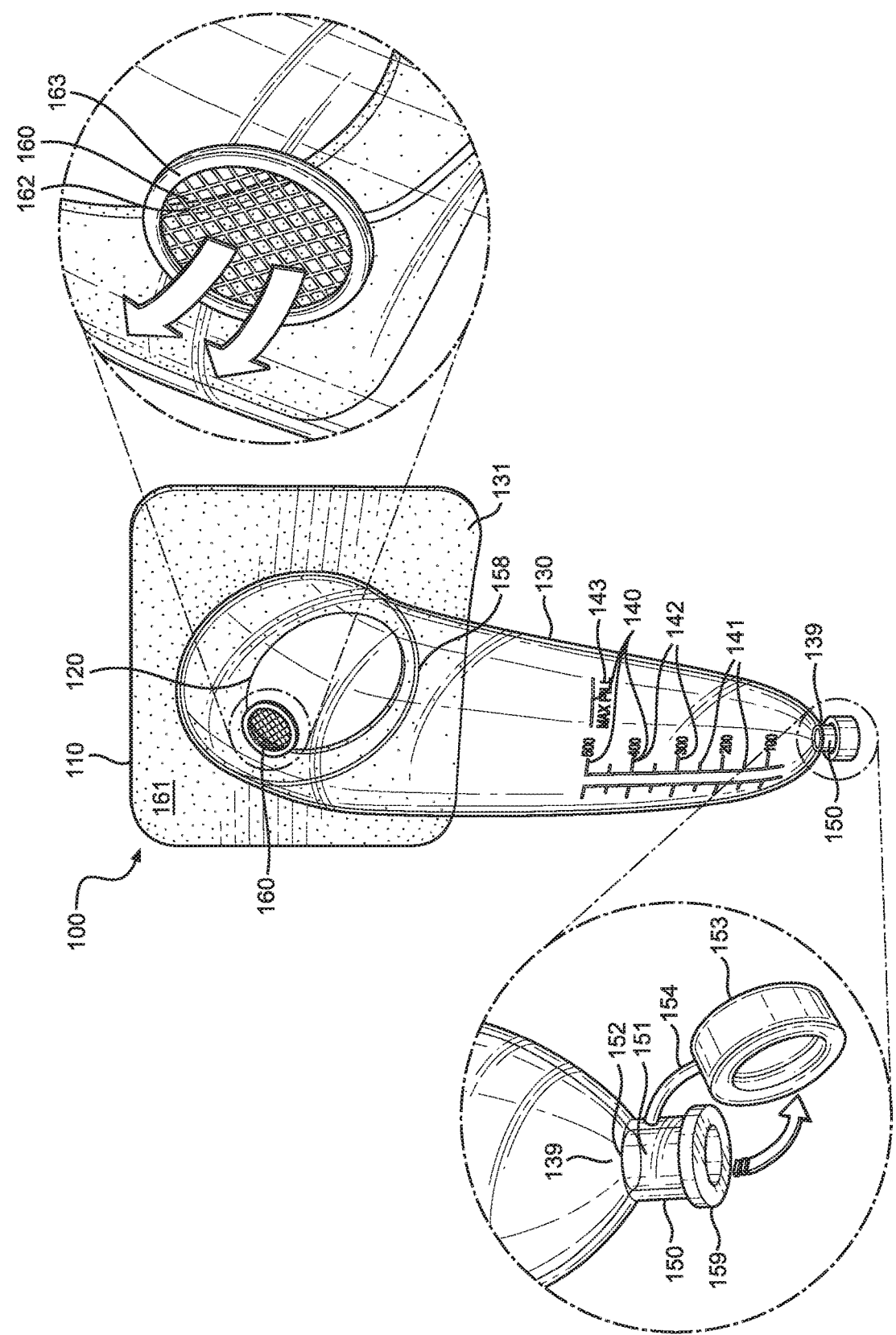
FIG. 1 shows a front perspective view of an embodiment of the external catheter, with a focus on a vent and a sealable drain.

Reference is made herein to the attached drawings. Like reference numerals are used throughout the drawings to depict like or similar elements of the external catheter. For the purposes of presenting a brief and clear description of the present invention, a preferred embodiment will be discussed as used for the external catheter. The figures are intended for representative purposes only and should not be considered to be limiting in any respect.

Referring now to FIG. 1, there is shown a front perspective view of an embodiment of the external catheter, with a focus on a vent and a sealable drain. The external catheter 100 comprises a planar base 110 with a central aperture 120 therethrough. In the shown embodiment, the planar base 110 is rectangular and the central aperture 120 is disposed in the center of the rectangle. In various other embodiments, the central aperture 120 can be offset from the center. In one embodiment, the central aperture 120 is sized to receive a penis of a wearer therethrough. It is therefore contemplated by the present disclosure that the central aperture 120 can be of a variety of diameters to accommodate a variety of penis widths and the central aperture 120 can be positioned in the base 110 in order to accommodate the wearer's anatomy. In one embodiment, the base 110 is flexible in order to allow the wearer free range of motion while wearing the external catheter 100. In a further embodiment, the flexible base 110 is configured to mimic a plurality of contours of the skin of a wearer when secured thereto, as further detailed below. As the shown embodiments of the external catheter 100 relate to wearing the external catheter 100 about the wearer's penis, one of ordinary skill in the art will understand that the flexible base 100 can be configured to mimic the contours of the skin as typically found around the pubic region of an individual.

A tubular member 130 is disposed on a front side 131 of the planar base 110 about the central aperture 120. In one embodiment, the tubular member 130 and the planar base 110 are composed of latex-free materials. In this manner, a wearer who may have latex allergies can utilize the external catheter 100 without fear of triggering the allergies through contact of the planar base 110 and/or the tubular member 130 with their skin. In one embodiment, the tubular member 130 is flexible in order to accommodate for the movement as well as the potential changing of size and shape of the wearer's penis during the term in which the external catheter 100 is worn.

The tubular member 130 is configured to store a fluid therein, such as urine. Thus, it is contemplated by the present disclosure that the tubular member 130 is composed of a leak-proof and fluid impermeable material. In one embodiment, the tubular member 130 further comprises indicia 140 configured to measure a volume of fluid contained therein. In the shown embodiment, the indicia 140 denote fifty-milliliter 141 and one hundred-milliliter 142 increments up to a total of five hundred milliliters. A "max fill" 143 indicia indicates the maximum volume of fluid to be contained within the tubular member 130 before the external catheter 100 needs to be replaced or the fluid drained from the tubular member 130. One of ordinary skill in the art will understand that the max fill 143 indicia, as well as the incremental indicia 141, 142 can correspond to a variety of volume capacities and is not limited to fifty, one hundred, and five hundred milliliter capacities.

In the shown embodiment, the tubular member 130 narrows toward an end disposed opposite to a connection point between the tubular member 130 and the planar base 110. A sealable drain 150 is disposed at a terminal end 139 of the tubular member 130. In one embodiment, the sealable drain 150 is disposed on an opposing end of the tubular member 130 from a point of attachment 158 between the tubular member 130 and the planar base 110. In the shown embodiment, the sealable drain 150 comprises a neck 151, a neck aperture 152 disposed through the neck 151, and a cap 153 configured to secure over a terminal end 159 of the neck 151 and thereby form a seal such that liquids are preventing from passing through the sealable drain 150.

The cap 153 is removably securable to the terminal end 159 of the neck 151. In the shown embodiment, the cap 153 is attached to the neck 151 of the sealable drain 150 by a flexible member 154. In such an embodiment, the flexible member 154 ensures that the cap 153 is not misplaced when removed from the terminal end 159 of the neck 151. In one embodiment, the cap 153 and the terminal end 159 of the neck 151 each comprise a complementary threading such that the cap 153 can be threadably secured to the neck 151. In the alternative shown embodiment, the sealable drain 150 comprises a click-lock closure wherein the cap 153 is removably secured to the terminal end 159 of the neck 151 by friction fit. In various embodiments, the sealable drain 150 is configured to removably secure to a foley catheter bag or similar drainage bag.

A vent 160 is disposed on a front surface 161 of the tubular member 130. The vent 160 enables air to flow into and out of the tubular member 130 and manages moisture therein. The vent 160 thereby enables air to flow out of the tubular member 130 as the tubular member 130 is being filled with a fluid. In this manner, pressure inside the tubular member 130 is in equilibrium with the outside environment and does not build as fluid is introduced. In the shown embodiment, the vent 160 comprises a mesh screen 162 with a ring 163 disposed around a perimeter thereof. In another embodiment, the vent 160 comprises a one-way valve. In the shown embodiment, the vent 160 is disposed opposite the central aperture 120. In such a configuration, the vent 160 is disposed far from the fluid as the fluid collects in the terminal end 139 of the tubular member 130. This configuration aids in preventing leaks and positions the vent 160 near the anatomy of the wearer for greater comfort.

Figure 2:
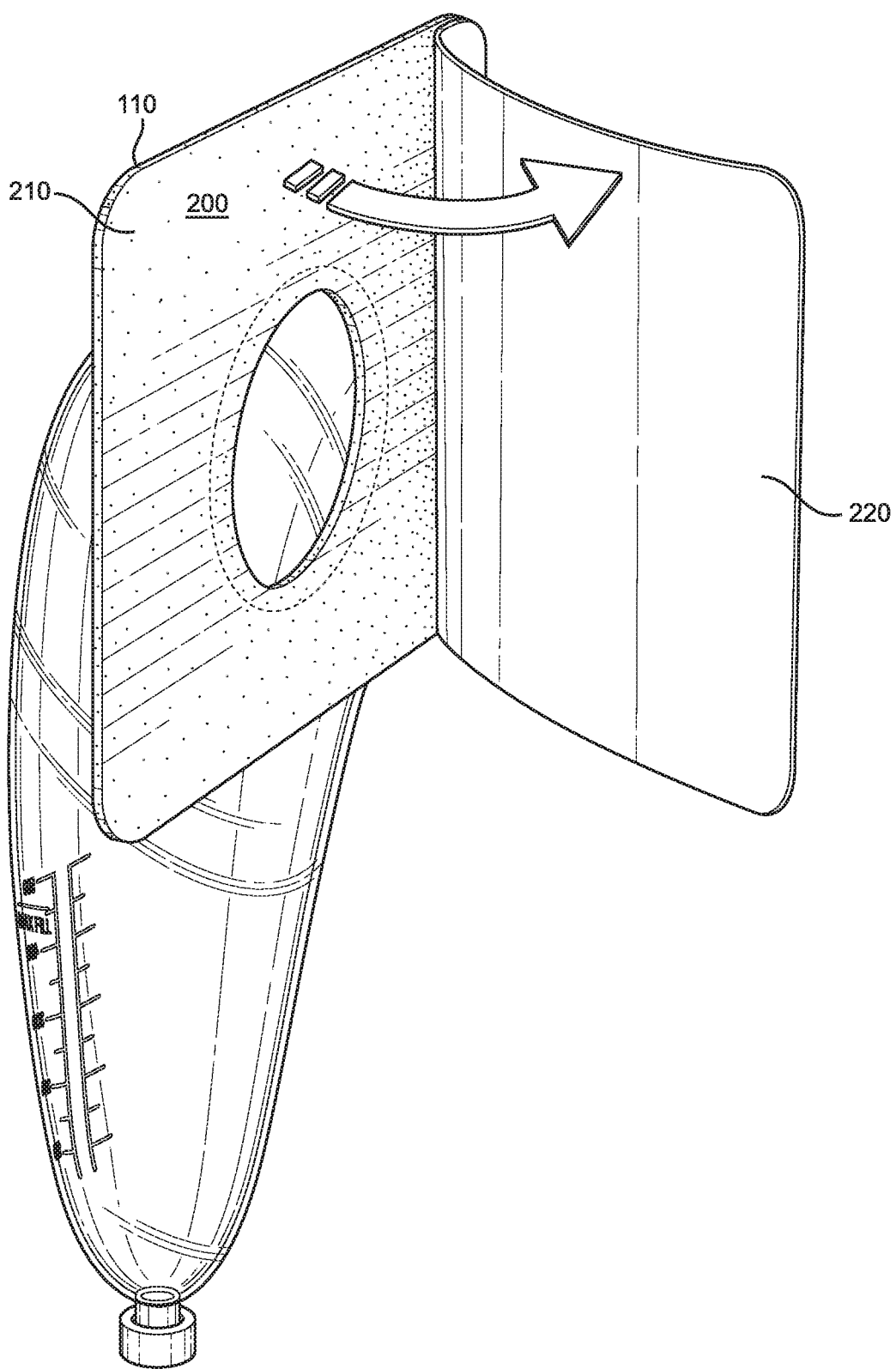
FIG. 2 shows a rear perspective view of an embodiment of the external catheter, with a focus on a removable adhesive backing material and an associated adhesive.

Referring now to FIG. 2, there is shown a rear perspective view of an embodiment of the external catheter, with a focus on a removable adhesive backing material and an associated adhesive. A back surface 200 of the base 110 comprises an adhesive material 210. The adhesive material 210 is configured to removably secure the base 110 to a skin of the wearer. In one embodiment, the adhesive material 210 is a gel-based adhesive to enable the adhesive to remain on the base 110 and establish a seal when secured to the skin. In various embodiments, the seal established is a watertight and airtight seal. The gel-based adhesive is hypoallergenic and latex-free to prevent allergic reactions when applied to the skin. In a further embodiment, the adhesive material 210 is a silicone adhesive to provide a material compatible with the skin that also allows the base 110 to be repositioned without losing the adhesive qualities. The silicone adhesive also provides the benefit of a waterproof seal that is permeable to air and is resistant to bacterial growth.

In one embodiment, an adhesive backing material 220 is removably secured to the adhesive material 210. The adhesive backing material 220 preserves the adhesive material 210 until the adhesive backing material 220 is removed, thereby exposing the adhesive material 210. The adhesive backing material 220 prevents debris and other undesirable elements from prematurely contacting the adhesive material 210. In the shown embodiment, both the adhesive material 210 and the adhesive backing material 220 cover the entire back surface 200 of the base 110. Further, in the shown embodiment, the adhesive backing material 220 is configured to be peeled away from the adhesive material 210 without the adhesive material 210 adhering thereto. In such a manner, the adhesive backing material 220 does not remove any adhesive material 210 from the base 110 when the adhesive backing material 220 is removed from the adhesive material 210.

Figure 3:
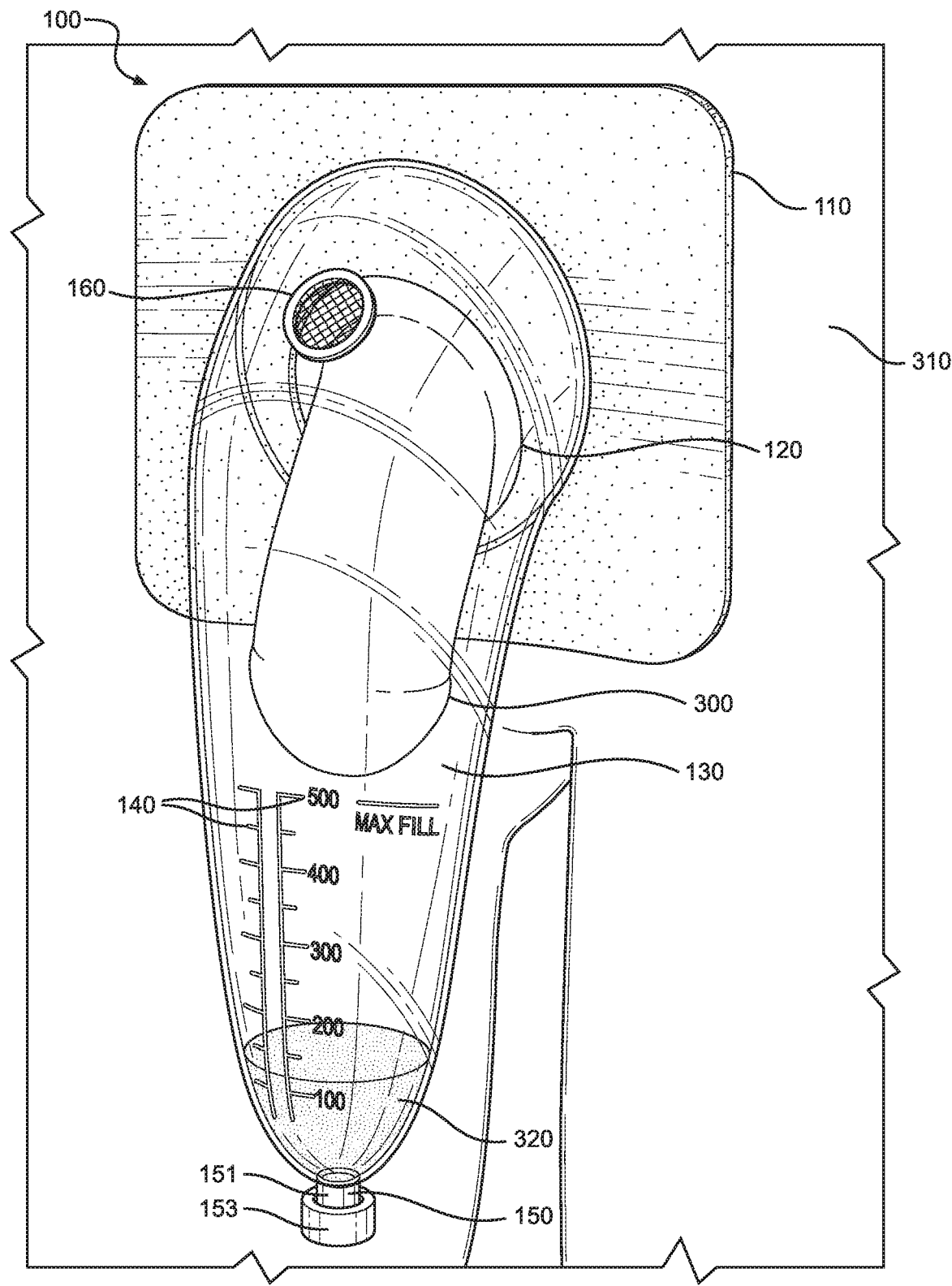
FIG. 3 shows a front perspective view of an embodiment of the external catheter, in use.

Referring now to FIG. 3, there is shown a front perspective view of an embodiment of the external catheter, in use. In operation a wearer can obtain an external catheter 100 and remove the adhesive backing material from the base 110, thereby exposing the adhesive material. The wearer can then insert their penis 300 into the tubular member 130 via the central aperture 120. The external catheter 100 can be rotated until the vent 160 is positioned away from the wearer's body, thereby allowing air to flow into and out of the tubular member 130. The adhesive material can then be pressed against the skin 310 of the pubic region of the wearer to secure the base 110 thereto. The wearer is able to remove and readjust the external catheter 100 until a comfortable fit is attained. The wearer can ensure that the sealable drain 150 is closed, such as by securing the cap 153 over the neck 151. Urine or other bodily fluids 320 can then be collected in the tubular member 130, and the indicia 140 can be utilized to measure the amount of fluid 320 captured and stored within the tubular member 130. As desired, the sealable drain 150 can be attached to a foley catheter bag or similar drainage bag and opened in order to drain the fluid 320 from the tubular member 130. The sealable drain 150 can then be closed and resealed, and thereby restore the external catheter 100 to a configuration wherein fluid 320 can be captured, collected, and stored again.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships h e illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An external catheter, comprising:
a planar base having a central aperture therethrough;
an entire back surface of the base comprising an adhesive material applied directly to the planar base;
the adhesive material is configured to removably secure the base to a skin;
an upper end of a tubular member disposed on a front side of the planar base about the central aperture, defining a connection point therebetween;
the planar base extends beyond a perimeter of the upper end of the tubular member about an entirety thereof;
the upper end of the tubular member comprises a larger diameter than a diameter of the central aperture, defining a continuous lip of the planar base extending radially inwardly from the connection point towards the central aperture;
the tubular member is configured to store a fluid therein;
a vent disposed on a front surface of the tubular member;
a sealable drain disposed at a terminal end of the tubular member; and
a removable adhesive backing material;
wherein the sealable drain comprises a clicklock closure;
wherein the tubular member further comprises indicia configured to measure a volume of fluid contained therein; and
wherein the vent is disposed opposite the central aperture.

2. The external catheter of claim 1, wherein the tubular member narrows towards an end opposite the connection point between the tubular member and the planar base.

3. The external catheter of claim 1, wherein the sealable drain further comprises a cap attached thereto by a flexible member.

4. The external catheter of claim 1, wherein the sealable drain is disposed on an opposing end of the tubular member from the connection point between the tubular member and the planar base.

5. The external catheter of claim 1, wherein the sealable drain is configured to removably secure to a Foley catheter bag.

6. The external catheter of claim 1, wherein the adhesive material is a gel-based adhesive.

7. The external catheter of claim 1, wherein the adhesive material is a silicone adhesive.

8. The external catheter of claim 1, wherein the central aperture is sized to receive a penis.

9. The external catheter of claim 1, wherein the planar base and tubular member are composed of latex-free materials.

10. The external catheter of claim 1, wherein the vent comprises a mesh screen affixed thereto.

11. The external catheter of claim 10, wherein the mesh screen is affixed to the vent via a ring disposed about a perimeter of the mesh screen.

12. The external catheter of claim 1, wherein the vent comprises a one-way valve.

13. The external catheter of claim 1, wherein the tubular member curves along a length thereof, such that the terminal end of the tubular member is disposed substantially perpendicular to the upper end of the tubular member.

14. An external catheter, consisting of:
a planar base having a central aperture therethrough, wherein the entire planar base is flexible;
an entire back surface of the base comprising an adhesive material applied directly to the planar base;
the adhesive material is configured to removably secure the base to a skin;
an upper end of a tubular member disposed on a front side of the planar base about the central aperture, defining a connection point therebetween;
a vent disposed on a front surface of the tubular member; and
a sealable drain located at a terminal end of the tubular member;
wherein the planar base extends beyond a perimeter of the upper end of the tubular member about an entirety thereof;
wherein the upper end of the tubular member comprises a larger diameter than a diameter of the central aperture, defining a continuous lip of the planar base extending radially inwardly from the connection point towards the central aperture; and
wherein the tubular member is configured to store a fluid therein.

15. The external catheter of claim 14, wherein the flexible planar base is configured to mimic the contours of the skin when secured thereto.

16. The external catheter of claim 15, wherein the skin is a pubic region of an individual.

* * * * *